United States Patent [19]

Ringwald

[11] 4,388,320

[45] Jun. 14, 1983

[54] 3-AMINOPROPOXYARYL DERIVATIVE IN THE TREATMENT OF TREMOR

[75] Inventor: Erwin Ringwald, Riehen, Switzerland

[73] Assignee: Sandoz Ltd., Basel, Switzerland

[21] Appl. No.: 354,454

[22] Filed: Mar. 3, 1982

[30] Foreign Application Priority Data

Mar. 9, 1981 [GB] United Kingdom ................ 8107305
Jan. 13, 1982 [GB] United Kingdom ................ 8200907

[51] Int. Cl.³ .......................................... A61Y 31/40
[52] U.S. Cl. ................................................ 424/274
[58] Field of Search ........................................ 424/274

[56] References Cited

U.S. PATENT DOCUMENTS 3,751,429 8/1973 Troxler et al. .

OTHER PUBLICATIONS

Hod et al., Postgrad. Med. J. 56, 346–347, (1980).
Ebadi M., Gen. Pharmac 11, (1980), 257.
Teravainen, H. et al., Neurology 27, (1977), 439.
Tyrer P. J., Drugs 20, (1980), 300–308, (1977).
Floru, L. et al., Int. Pharmacopsychiat. 14 (1979) 149 (Abstract).

Primary Examiner—Stanley J. Friedman
Attorney, Agent, or Firm—Gerald D. Sharkin; Robert S. Honor

[57] ABSTRACT

The compound 4-(2-benzyloxy-3-tert-butylaminopropoxy)-2-methylindole is useful in the treatment of tremor, especially of essential (familiary) tremor.

8 Claims, No Drawings

3-AMINOPROPOXYARYL DERIVATIVE IN THE TREATMENT OF TREMOR

Sandoz U.K. Patent Specification No. 1,575,510 discloses and claims the compound of formula I

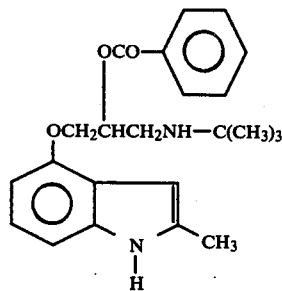

i.e. 4(2-benzoyloxy-3-tert-butylaminopropoxy)-2-methylindole.

The compound is indicated to have pharmacological activity. In particular, it is indicated to exhibit a blocking effect on the adrenergic β-receptors (a β-blocking effect), additionally an antiarrhythmic effect, and to inhibit lipolysis and glycogenolysis induced by isoproterenol, and to be therefore indicated for use as a β-blocking agent, i.a. in the prophylaxis and therapy of coronary diseases, especially in the treatment of Angina pectoris, in the treatment of the hyperkinetic heart syndrome and of the conditions resulting from a muscular hypertrophic subvalvular aortic stenosis.

The present invention relates to a new use of this compound.

Tremor is a very largely disseminated affliction of various etiology; it can be e.g. of essential (familiary) origin. Various drugs are used in the treatment of tremor, however with questionable results. Although the use of some β-adrenoceptor blocking agents against tremor, e.g. of propranolol, is known, conflicting results have been obtained, while some agents, e.g. alprenolol, oxprenolol, timolol, etc. are inactive.

It has now been found that the compound of formula I surprisingly is useful in the treatment of tremor, especially of essential (familiary) tremor, as indicated by clinical observations as described below.

In one clinical study 6 patients with constant essential (familiary) tremor were given for 4 weeks once-a-day in the morning a capsule containing 1 to 8 mg of the compound of formula I in hydrogen malonate form. The dosage was increased gradually over the first two weeks of the study.

The improvement in tremor during treatment is shown in table 1:

TABLE 1

| Total number of patients | Improvement | | | | | | | |
|---|---|---|---|---|---|---|---|---|
| | after 2 weeks | | | | after 4 weeks | | | |
| | Ma | Mo | Mi | No | Ma | Mo | Mi | No |
| 6 | 2 | 4 | — | — | 3 | 3 | — | — |

Ma = Marked
Mo = Moderate
Mi = Minimal
No = No change

It can be seen that all patients gained benefit. Moreover, the degree of improvement was either marked or moderate. It was additionally observed that the beneficial effect lasted the whole day. The effect observed was remarkably free of side effects. No hypotension and no bradycardia were observed during treatment.

The result of a further, similar study with 4 patients with essential (familiary) tremor treated for 4 weeks with 1 to 12 mg per day of the compound of formula I in hydrogen malonate form is indicated in table 2:

TABLE 2

| Number of patients showing improvement | | | |
|---|---|---|---|
| very good | good | moderate | no |
| 2 | 2 | — | — |

It can be seen that marked improvement was observed in all 4 patients. Improvement could be observed already after one week of treatment, maximum improvement after 2 weeks. Again, exceptionally few side effects, e.g. no hypotension and no bradycardia, were observed.

These results were confirmed in still another clinical study involving 6 patients with essential (familiary) tremor treated for 4 weeks with 4 to 12 mg per day of the compound of formula I in hydrogen malonate form.

The improvement in tremor during treatment is shown in table 3:

TABLE 3

| Number of patients showing improvement | | | |
|---|---|---|---|
| very good | good | moderate | no |
| 3 | 3 | — | — |

It can be seen that very good or good improvement was observed in all patients. Again, no hypotension and no bradycardia were observed.

In view of the rarity of the condition to be treated, the clinical studies described above had to be effected with a limited number of patients; the results nonetheless unambiguously demonstrate an impressive improvement after administration of the compound of formula I.

The compound of formula I is therefore useful as an antitremor agent.

For the above-mentioned anti-tremor use, the dosage will of course vary depending on the mode of administration and therapy desired. However, in general a daily dosage of from about 0.03 mg/kg to about 0.25 mg/kg animal body weight is satisfactory, conveniently given in divided doses 2 to 4 times a day or as part of a sustained release form. For the larger mammal the total daily dosage is in the range of from about 1 mg to about 16 mg, preferably about 2 mg to about 12 mg, especially about 2 mg to about 4 mg, and dosage forms suitable for oral administration comprise from about 0.25 mg to about 8 mg of the compound admixed with a solid or liquid pharmaceutical carrier or diluent.

Preferred is the use against essential (familiary) tremor.

Once-a-day administration is preferred.

The compound is better tolerated than anticholinergics, its anti-tremor effect has a more rapid onset of activity and its administration is simpler. It is better tolerated than other β-adrenoceptor blocking agents, e.g. propranolol. It does thus not induce hypotension or bradycardia; however, it leads to a normalization of blood pressure and heart rate in patients with underlying hypertension or tachycardia. Additionally, it does not significantly influence the P-Q wave in the electrocardiogramm. It can thus be considered as being exceptionally safe.

The tolerability of the compound was also studied using standard tests. For example, the acute toxicity of the compound of formula I in hydrogen malonate form is as follows:

|  | LD$_{50}$ (mg/kg) | |
| --- | --- | --- |
|  | i.v. | p.o. |
| Mouse | 11 | 242 |
| Rat | 9 | 1009 |
| Rabbit | 7 | 334 |

The free base form of the compound of formula I may be converted into acid addition salt forms and vice-versa in conventional manner.

The compound of formula I can, by virtue of the asymmetric carbon atom in the position $\beta$ to the oxygen atom bound to the indole nucleus, exist in the form of optically active isomers or as a racemate. The compound of formula I is preferably in racemic or (S)-enantiomeric form.

The compound of formula I may be obtained in conventional manner, e.g. by benzoylating 4-(2-hydroxy-3-tert-butylaminopropoxy)-2-methylindole.

The compound of formula I may be administered in free base form or in pharmaceutically acceptable acid addition salt form. Such acid addition salt forms are known, exhibit the same order of activity as the free base forms and are readily prepared in conventional manner. Representative acid addition salt forms include the fumarate, hydrogen fumarate and hydrogen malonate.

Conveniently the compound of formula I is administered in the form of a pharmaceutical composition comprising the compound of formula I in free base form or in pharmaceutically acceptable acid addition salt form, in association with a pharmaceutical carrier or diluent. Such compositions are known and may be formulated in conventional manner so as to be, for example, a solution or a tablet.

The following Examples illustrate the invention:

EXAMPLE 1

Capsule

A representative formulation suitable for oral administration is a capsule prepared by standard encapsulating techniques, which contains the following and is useful for oral administration 1 to 4 times a day as an anti-tremor agent.

| Ingredient | Capsule (mg) |
| --- | --- |
| Compound of formula I (in hydrogen malonate form, i.e. 1.273 mg) | 1.0 |
| lactose | 200.5 |
| corn starch | 140.0 |
| stearic acid | 7.0 |
| silicium dioxyde | 1.5 |
| total | 350.0 |

EXAMPLE 2

Tablet

The following composition may be formulated using standard tabletting techniques and is useful for administration 1 to 4 times a day as an anti-tremor agent.

| Ingredient | Tablet (mg) |
| --- | --- |
| Compound of formula I (in hydrogen malonate form, i.e. 1.273 mg) | 1.0 |
| polyvinylpyrrolidone | 3.0 |
| lactose | 127.7 |
| corn starch | 15.0 |
| talcum | 1.5 |
| collodial silicon dioxide | 0.3 |
| magnesium stearate | 1.5 |
| total | 150.0 |

EXAMPLE 3

Tablet

The following composition may be formulated using standard tabletting techniques and is useful for administration 1 to 4 times a day as an anti-tremor agent.

| Ingredient | Tablet (mg) |
| --- | --- |
| 4-(2-benzoyloxy-3-tert-butylaminopropoxy)-2-methylindole hydrogen malonate | 1.273 |
| lactose | 3.9 |
| ricinoil | 1.3 |
| lactose | 1.1 |
| ferric oxide pigment | 0.055 |
| lactose | 98.0 |
| sodium carboxymethyl starch (Primojel) | 4.2 |
| hydroxypropylmethyl cellulose (Pharmacoat 603, Shinetsu Chemical) | 6.5 |
| malonic acid | 0.015 |
| corn starch | 13.0 |
| ricinoil | 0.65 |
| total | 130.0 |

I claim:

1. A method of treating tremor in animals comprising administering 4-(2-benzoyloxy-3-tert-butylaminopropoxy)-2-methylindole in free base form or in pharmaceutically acceptable acid addition salt form to an animal in need of such treatment.

2. A method of treating tremor in animals suffering therefrom comprising administering to an animal in need of such treatment a therapeutically effective amount of a compound as defined in claim 1.

3. A method of claim 1, wherein the condition to be treated is essential (familiary) tremor.

4. A method of claim 1, wherein the daily dosage is from 1 mg to 16 mg.

5. A method of claim 5, wherein the daily dosage is from 2 mg to 12 mg.

6. A method of claim 6, wherein the daily dosage is from 2 mg to 4 mg.

7. A method of claim 4 to 6, wherein the daily dosage is administered 2 to 4 times a day in unit dosage form.

8. A method of claim 4 to 6, wherein the dosage is administered as part of a sustained release form.

* * * * *